(12) United States Patent
Guthrie

(10) Patent No.: US 10,222,347 B2
(45) Date of Patent: Mar. 5, 2019

(54) METHOD AND DEVICE FOR MEASURING ION CONCENTRATION

(71) Applicant: NATURION PTE. LTD., Bukit, Merah Central (SG)

(72) Inventor: Warren Edwin Guthrie, West Olive, MI (US)

(73) Assignee: NATURION PTE. LTD., Merah Central (SG)

( * ) Notice: Subject to any disclaimer, the term of this patent is extended or adjusted under 35 U.S.C. 154(b) by 23 days.

(21) Appl. No.: 15/467,670

(22) Filed: Mar. 23, 2017

(65) Prior Publication Data

US 2017/0276639 A1 Sep. 28, 2017

Related U.S. Application Data

(60) Provisional application No. 62/313,873, filed on Mar. 28, 2016.

(51) Int. Cl.
*G01N 27/416* (2006.01)
*G01N 27/70* (2006.01)
*H01J 49/02* (2006.01)

(52) U.S. Cl.
CPC ........... *G01N 27/416* (2013.01); *G01N 27/70* (2013.01); *H01J 49/025* (2013.01)

(58) Field of Classification Search
CPC ...... G01N 27/416; G01N 27/70; H01J 49/025
USPC ........................................................ 324/693
See application file for complete search history.

(56) References Cited

U.S. PATENT DOCUMENTS

| 3,478,205 | A |   | 11/1969 | Sporek |   |
|---|---|---|---|---|---|
| 4,064,548 | A |   | 12/1977 | Best et al. |   |
| 4,271,357 | A | * | 6/1981 | Bradshaw | G01N 27/68 250/282 |
| 6,176,977 | B1 |   | 1/2001 | Taylor et al. |   |
| 6,785,114 | B2 |   | 8/2004 | Gorczyca et al. |   |
| 6,974,560 | B2 |   | 12/2005 | Taylor et al. |   |
| 7,897,117 | B2 |   | 3/2011 | Taylor et al. |   |
| 8,771,599 | B2 |   | 7/2014 | Funabiki et al. |   |
| 8,895,919 | B2 | * | 11/2014 | Nishino | H01T 23/00 250/285 |

(Continued)

FOREIGN PATENT DOCUMENTS

| CN | 205303948 U | 6/2016 |
|---|---|---|
| JP | H08 255669 A | 10/1996 |

(Continued)

OTHER PUBLICATIONS

Survey Meters, retrieved from the Internet on May 17, 2018, URL: https://www.nde-ed.org/EducationResources/CommunityCollege/RadiationSafety/radiation_safety_equipment/SurveyMeters.htm, webpage could be accessed on Aug. 11, 2014 (see htts://web.argive.org/web/20140811092610/https://www.nde-ed.org/EducationResources/CommunityCollege/RadiationSafety/radiation_safety_equipment/SurveyMeters.htm).

*Primary Examiner* — Reena Aurora
(74) *Attorney, Agent, or Firm* — McGarry Bair PC

(57) ABSTRACT

A method and device for measuring ion concentration in a defined space including disposing at least one conductive surface in a defined space, generating a flow of ions from an ion generator having an anode and a cathode into the defined space, measuring one of voltage across or direct current (DC) through a resistor connected between the cathode and the at least one conductive surface, and determining ion concentration in the defined space based upon a proportionality of ion concentration to the measured voltage or current.

13 Claims, 4 Drawing Sheets

(56) References Cited

U.S. PATENT DOCUMENTS

| | | |
|---|---|---|
| 8,901,506 B2 | 12/2014 | Fukada |
| 2012/0313005 A1 | 12/2012 | Nishino |

FOREIGN PATENT DOCUMENTS

| | | |
|---|---|---|
| JP | 2002189017 A | 7/2002 |
| JP | 2003036954 A | 2/2003 |
| JP | 2004 053555 A | 2/2004 |
| JP | 2005005049 A | 1/2005 |
| WO | 2015/146456 A1 | 1/2015 |

* cited by examiner

METHOD AND DEVICE FOR MEASURING ION CONCENTRATION

CROSS REFERENCE TO RELATED APPLICATIONS

This application claims the benefit of U.S. Provisional Application Ser. No. 62/313,873 filed Mar. 28, 2016, which is incorporated herein by reference in its entirety.

BACKGROUND OF THE INVENTION

The present invention relates broadly to a device and method for measuring the flow of ions injected into a defined space, in particular negative ions.

SUMMARY OF THE INVENTION

In one aspect, the disclosure relates to a method of measuring ion concentration in a defined space, including disposing at least one conductive surface in a defined space, generating a flow of ions from an ion generator having an anode and a cathode into the defined space, measuring one of voltage across or direct current (DC) through a resistor connected between the cathode and the at least one conductive surface, and determining ion concentration in the defined space based upon a proportionality of ion concentration to the measured voltage or current.

In another aspect, the disclosure relates to a device for measuring ion concentration in a defined space, including a power supply, an ion generator having an anode and a cathode connected to the power supply, a fan to move air in a path between the anode and the cathode to a defined space, at least one conductive surface in the defined space, a resistor connected between the cathode and the at least one conductive surface, and a measuring circuit connected to the resistor for measuring one of voltage across or DC current through the resistor. The measured one of voltage across or direct current (DC) through the resistor is proportional to ion concentration in the defined space.

DESCRIPTION OF THE PREFERRED EMBODIMENT

Figure 1:
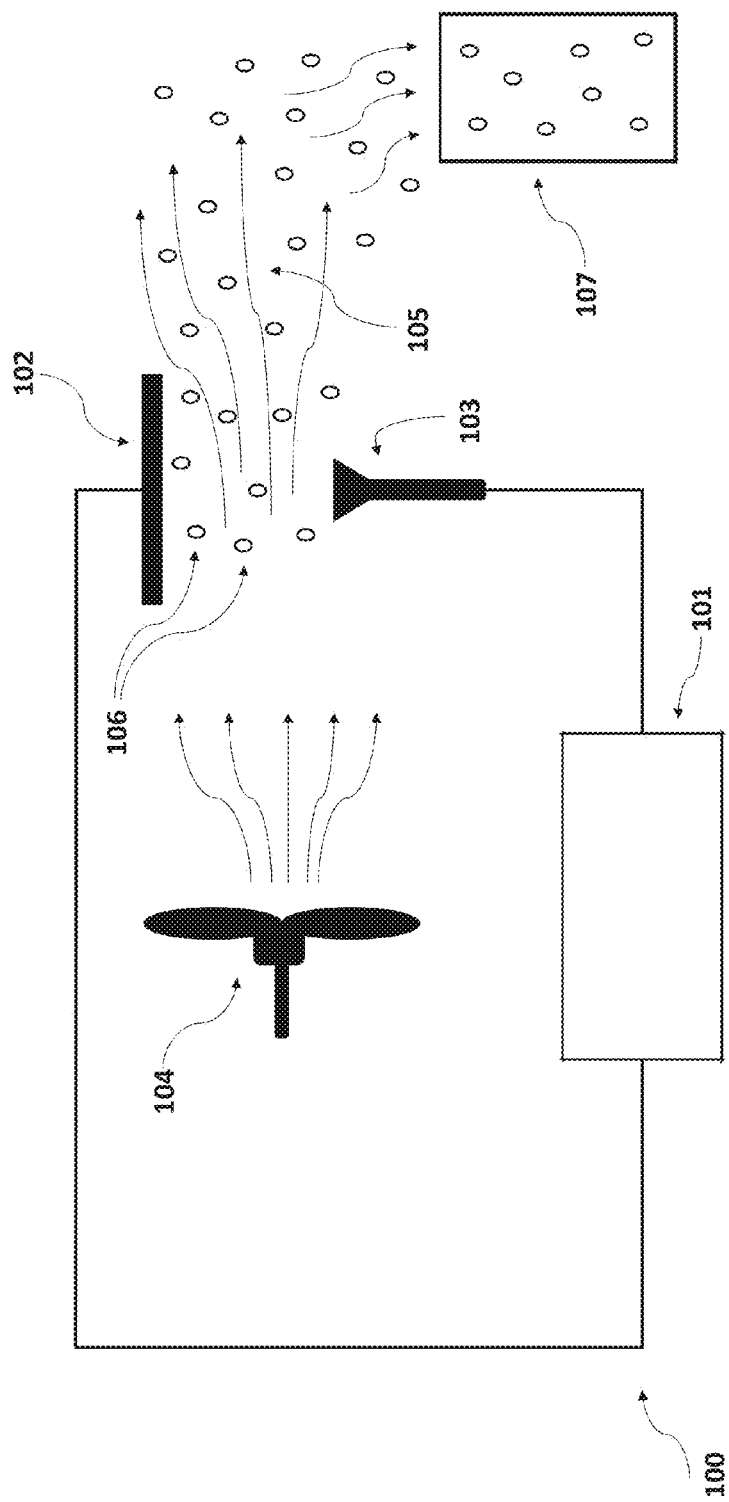
FIG. 1 shows a prior art schematic drawing of a device for injecting ions into a stream of air and measuring ion concentration near the ion source.

While "a set of" various elements will be described, it will be understood that "a set" can include any number of the respective elements, including only one element. Also as used herein, while sensors can be described as "sensing" or "measuring" a respective value, sensing or measuring can include determining a value indicative of or related to the respective value, rather than directly sensing or measuring the value itself. The sensed or measured values can further be provided to additional components. For instance, the value can be provided to a controller module or processor, and the controller module or processor can perform processing on the value to determine a representative value or an electrical characteristic representative of said value.

Additionally, while terms such as "voltage", "current", and "power" can be used herein, it will be evident to one skilled in the art that these terms can be interchangeable when describing aspects of the electrical circuit, or circuit operations.

Connection references (e.g., attached, coupled, connected, and joined) are to be construed broadly and can include intermediate members between a collection of elements and relative movement between elements unless otherwise indicated. As such, connection references do not necessarily infer that two elements are directly connected and in fixed relation to each other. In non-limiting examples, connections or disconnections can be selectively configured to provide, enable, disable, or the like, an electrical connection between respective elements.

Aspects of the present disclosure relate to a device and method for measuring injecting ions traveling through a protected space. Aspects of the disclosure will be better understood and readily apparent to one of ordinary skill in the art from the following written description, by way of example only, and in conjunction with the drawings. The exemplary drawings are for purposes of illustration only and the dimensions, positions, order and relative sizes reflected in the drawings attached hereto can vary.

Negative air ion generation can be used as a means to clean air. The negative air ion generation operates by adding electrons to air molecules and then these negatively charged particles bond to air-borne pollutants and subsequently move to more positively charged surfaces like walls and floors. The overall process moves pollutants from the air in a protected space to another place or space that can be easily cleaned with traditional methods.

Since the process consists of projecting a stream of electrons that are attached to air molecules, there is a resulting negative current flow from the ion generator into the protected space. Higher current flow results in more effective cleaning. Thus, cleaning effectiveness can be indicated by or related to the current flow of the ion generator. Various factors can reduce current flow such as inadequate grounding of the ionizer, low anode Voltage, blocked vents, or the like. If any factor reduces the electron flow, the resulting process has a reduced effectiveness. The air cleaning process may also be compromised if the ions do not reach the intended space. This can occur if the ion current is short circuited in way that they reach the ion generator circuit without traveling through the intended space. Aspects of the disclosure relates to determining the effectiveness of projecting ions into a defined space based on measurement of current from the ion generator through conductive surfaces in the protected space.

Non-limiting aspects of ion measurement is can be based on measuring ion density, for example, in millions of ions per cubic centimeter. One such method is the Gerdien Tube, which measures the rate of charge removal in a certain volume due to the dissipation of ions in that volume. Additional various non-limiting methods can be utilized, but generally measure the ion density local to the metering device. When the measurement(s) of ion density do not take into account the path of ion flow, they may not accurately reflect the rate of ion flow through the protected space.

FIG. 1 illustrates the prior art. A device 100 can operate to inject ions into a stream of air 105. The device 100 uses a high Voltage source 101 connected to a cathode 102 and anode 103. Negative ions 106 are produced in the region between the anode 103 and cathode 102. A fan 104 blows the ions contained in a stream of air 105. Another device 107 measures the concentration of ions in a region surrounding the ion generator.

Figure 2:
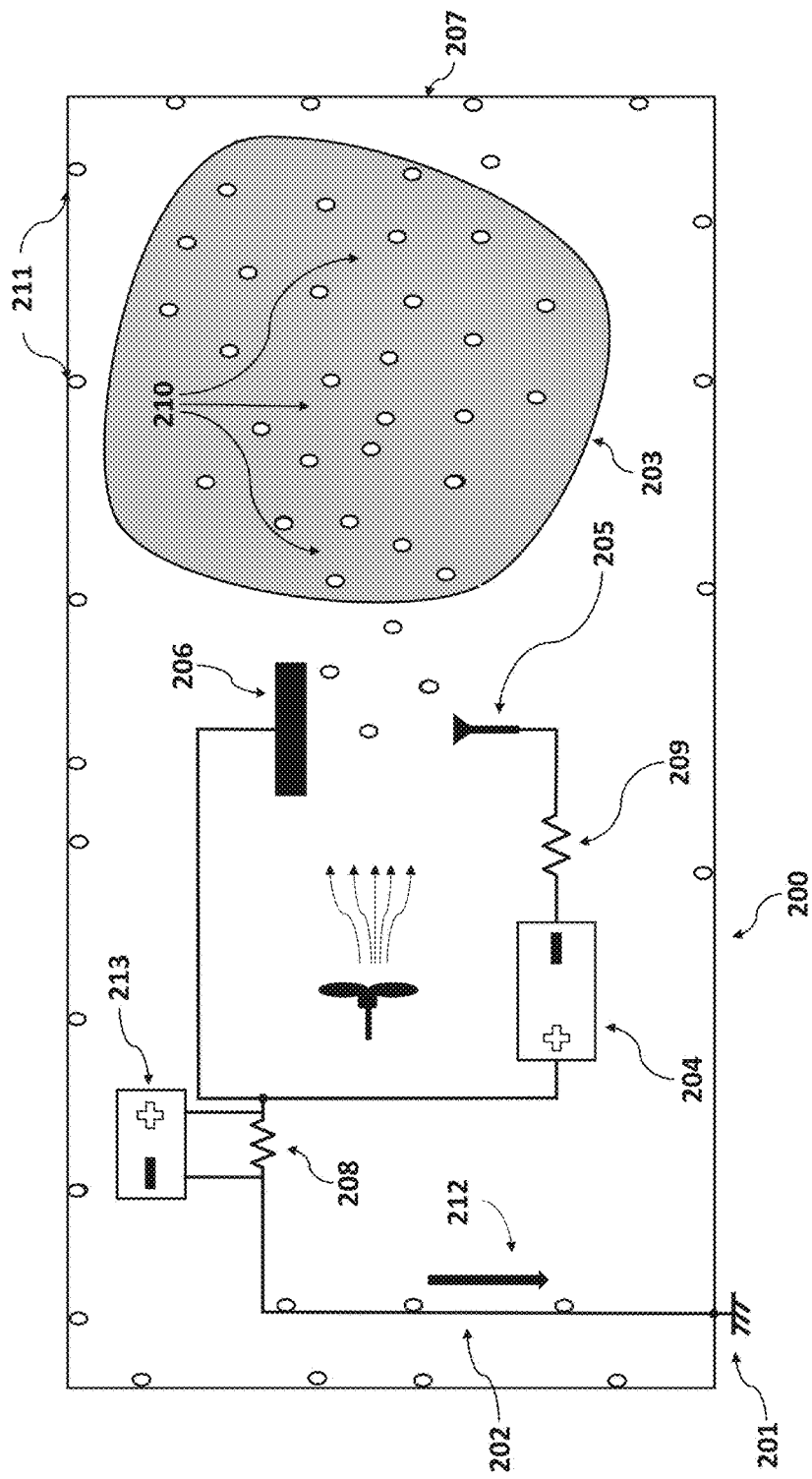
FIG. 2 shows an electrical diagram, emphasizing current flow from an ion generator, in accordance with various aspects described herein.

FIG. 2 illustrates an ion generator 200 in accordance with the current disclosure that injects a stream of ions 210 into air. The ion generator 200 includes a high Voltage power supply 204, an anode 205, a cathode 206, and a safety resistor 209. As used herein, a "safety resistor" 209 is a current limiting resistor that prevents or limits a current in the occurrence of a short circuit or fault. The high Voltage power supply 204 supplies power between the anode 205 and the cathode 206 to generate the ions 210. As shown, a fan can flow the air between the anode 205 and the cathode 206 to move or carry the ions 210 away from the anode 205 or cathode 206. The ions 210 flow through a protected space 203 to at least one conductive surface 207 around or within the protected space. In this sense, the at least one conductive surface 207 can be in the air path of the ions 210 or ion flow.

The conductive surfaces 207, in response to ions 210 contacting the surfaces 207, conduct or support a flow of electrons 211. The flow of electrons 211 causes an electric current 212 to flow through a second resistor 208, connected, via a conductor 202, in series between the conductive surfaces 207 and the cathode 206 or power supply 204. The current in the second resistor 208 produces a Voltage on the second resistor 208 that can be subsequently measured by a circuit 213, such as a voltmeter. The Voltage measured by the circuit 213 can be proportional to the number of electrons (and hence number ions) that flow through the protected space 203. Optionally, the conductive surfaces 207 can be connected to Earth ground 201.

Figure 3:
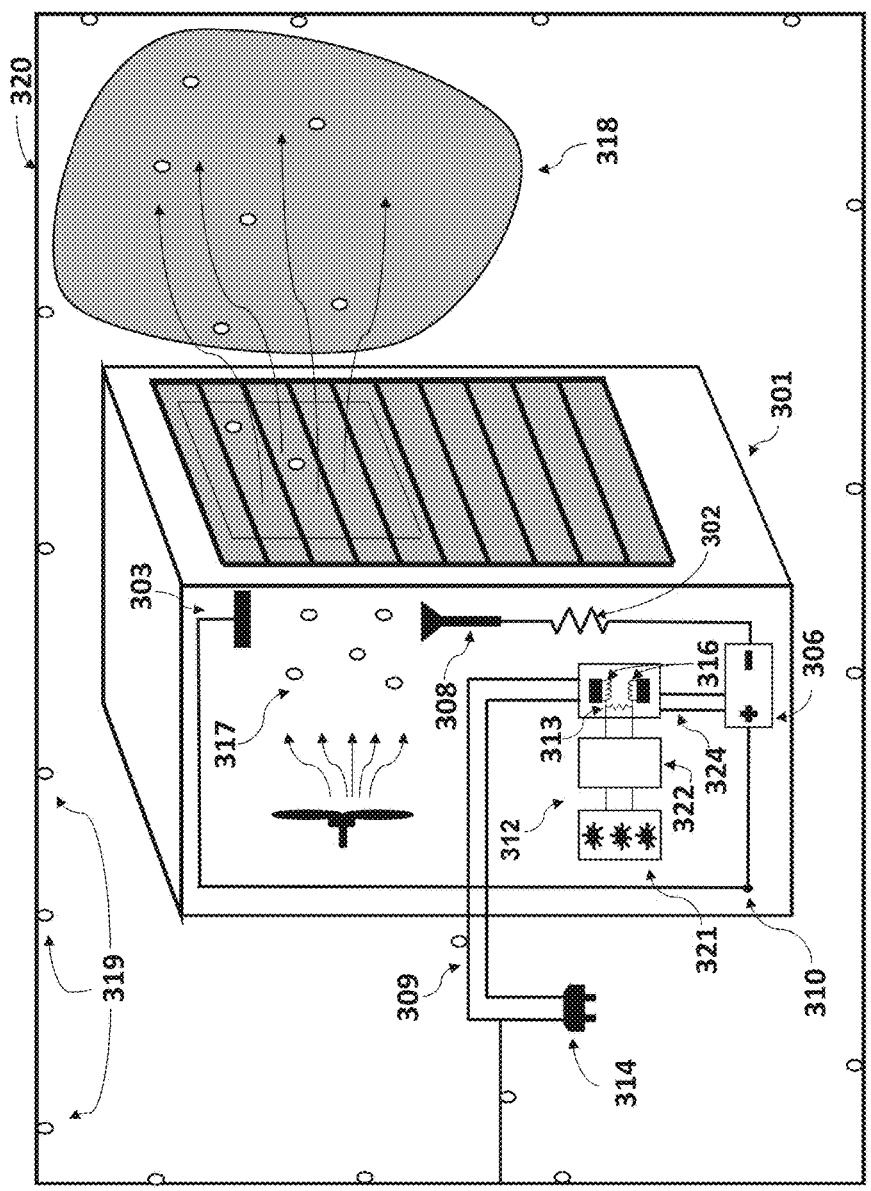
FIG. 3 shows a diagram of the electric circuits in accordance with various aspects described herein.

FIG. 3 illustrates a diagram for another ion generator 301 including aspects of the disclosure. Aspects of FIG. 3 are similar to earlier-described components, and thus, similar descriptions are applicable here, unless otherwise described. A difference between the earlier ion generator 200 and the ion generator 301 is that the ion generator 301 utilizes a mains power supply 314. The ion generator 301 can include a high Voltage power supply 306, anode 308, cathode 303, and safety resistor 302. The ion generator 301 can further include a power supply 312 having a direct current (DC) isolation barrier 316, shown as a transformer. The power supply 312 includes a high value resistor 313 across the DC isolation barrier 316 which produces a DC Voltage proportional to a flow of ions 317 through a protected space 318. The DC Voltage is measured by a circuit 322 which further indicates the magnitude of ion flow, for instance, by way of indicator lights 321. In one non-limiting aspect, the ion concentration can be determined by way of comparing the Voltage (or current) measured with a look up table.

The protected space 318 can includes at least one conductive surface 320 in or around it to support the flow of electrons 319, as described above, and connected with the mains power 314 by way of a conductive connection 309. The electrons flow 319 through electrical components form a closed path. The closed path can include, but is not limited to, the following elements, for instance, in electrical series: the high Voltage power supply 306 (negative terminal), the protection or safety resistor 302, the anode 308, the negative ions 317 between the anode 308 or near the cathode 303, the negative ions 317 in the protected space 318, the negative ions 319 on the conductive surface 320, the mains power connection 309, the resistor 313 across the isolation barrier 316, and a conductive connection 324 to the high Voltage power supply 306. The high Voltage power supply 306 can further be connected with the cathode 303 by way of a cathode connection 310.

Figure 4:
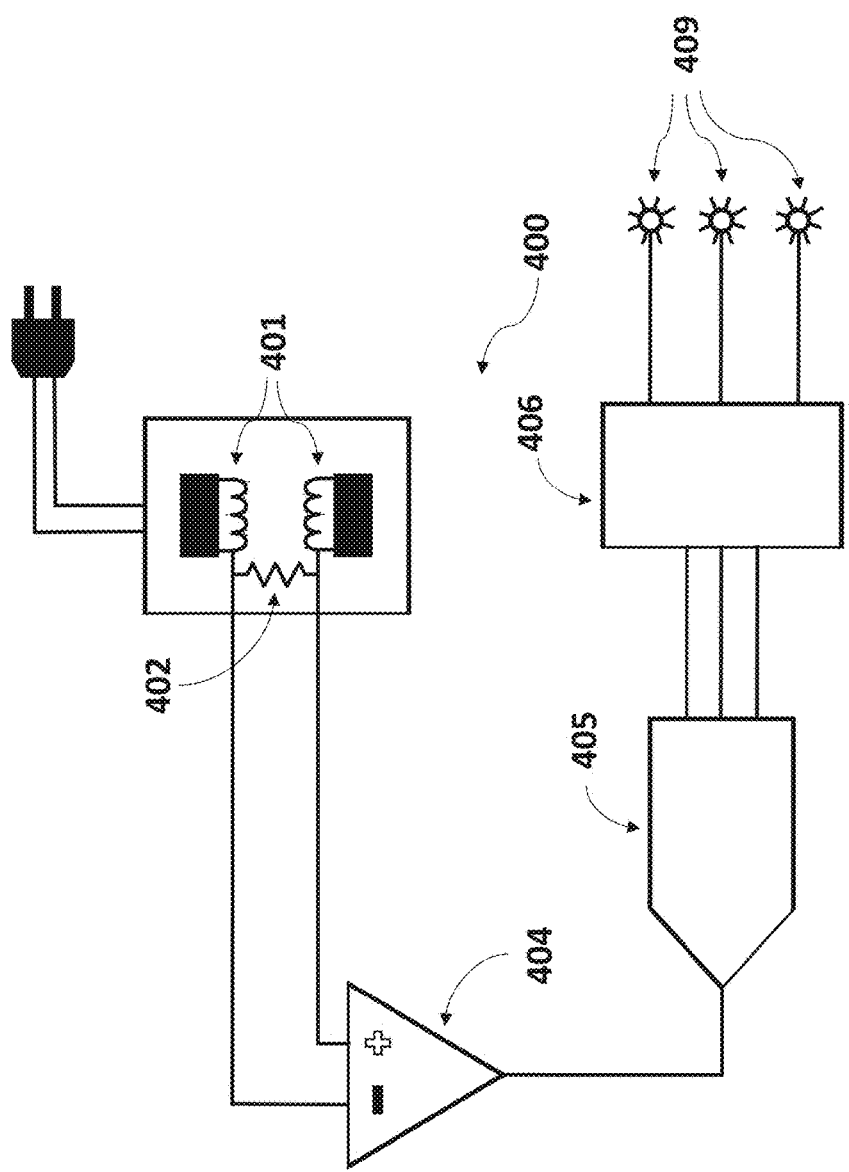
FIG. 4 diagrams the ion current flow measuring circuit, in accordance with various aspects described herein.

FIG. 4 illustrates a schematic diagram of the relevant parts of the ion current measurement circuit 400. The schematic shows a high frequency transformer 401 that blocks DC and transfers alternating current (AC) power required to operate the ionizer circuits (not shown). A bridge resistor 402 allows ion current (which is DC) to flow around the transformer 401. A Voltage from the DC ion current is developed on the resistor 402 and can be amplified by a differential amplifier 404. An analog-to-digital converter 405 can provide a digital indication of the ion flow current to a processor 406 which can in turn illuminate at least one indicator lamp 409. Thus, the analog-to-digital converter 405, the processor 406, or the indicator lamps 409 can effectively or operably display an indication (such as brightness or illuminated/unilluminated indication) of the magnitude of the ion flow, as described herein.

Aspects of the disclosure can effectively operate to measure ions that travel through a space that contains or is surrounded by conductive surfaces. By establishing an electrical connection from these conductive surfaces to the ion generator cathode, it can be assured that the measured current is from ion flow.

The ion current flow through the protected space is DC and typically very small, on the order of 10 uA. As such, measurement with a direct connection through a resistor to mains would be extraordinarily difficult since the small DC current would be combined with a large AC current that powers the ion generation circuitry. One aspect of the disclosure resolves this difficulty by transferring power from the mains through a DC isolation barrier (in one non-limiting example, as might be part of a switch-mode power supply). As described herein, power is transferred using a high frequency across the barrier, thereby allowing or enabling the current from the ion flow. The DC flow is measured separately from current required to operate the ion generator circuitry, which is AC.

Thus, in one non-limiting example of the disclosure, the above-described aspects provides a novel alternative to measurement of ions by measuring the useful flow of ions through a protected space. Non-limiting aspects of the disclosure can be included wherein the method is based on 1) establishing a connection from the cathode of the high Voltage source used in the ion generator, to conductive surfaces within a protected space, and 2) measuring DC current flow through the connection referred to in step 1). The method can use a measurement of current flowing though conductive surfaces surrounding or within a protected space to the ion source's high Voltage power supply cathode to indicate the ion flow through the protected space.

In another non-limiting method of measuring ion concentration in a defined space can include 1) disposing at least one conductive surface in a defined space, 2) generating a flow of ions from an ion generator having an anode and a cathode into the defined space, 3) measuring one of voltage across or DC current through a resistor connected between the cathode and the at least one conductive surface, and 4) determining ion concentration in the defined space based upon a proportionality of ion concentration to the measured voltage or current.

The sequence described herein is for exemplary purposes only and is not meant to limit the method in any way as it is understood that the portions of the method can proceed in a different logical order, additional or intervening portions can be included, or described portions of the method can be divided into multiple portions, or described portions of the method can be omitted without detracting from the described method.

Many other possible embodiments and configurations in addition to that shown in the above figures are contemplated by the present disclosure. To the extent not already described, the different features and structures of the various embodiments can be used in combination with each other as desired. That one feature cannot be illustrated in all of the embodiments is not meant to be construed that it cannot be, but is done for brevity of description. Thus, the various features of the different embodiments can be mixed and matched as desired to form new embodiments, whether or not the new embodiments are expressly described. Combinations or permutations of features described herein are covered by this disclosure.

In one non-limiting aspect of the disclosure, embodiments of the invention can include any permutation or combination of at least a subset of the following aspects: a power supply, an ion generator having an anode and a cathode connected to the power supply, and a fan to move air in a path between the anode and the cathode to a defined space, at least one conductive surface in the defined space, a resistor connected between the cathode and the at least one conductive surface, a measuring circuit connected to the resistor for measuring voltage across or DC current through the resistor, wherein the measured one of voltage across or direct current (DC) through the resistor is proportional to ion concentration in the defined space, a DC isolation barrier between the power supply and the ion generator, wherein the resistor is connected across the isolation barrier, a display connected to the measuring circuit to indicate ion concentration in the defined space, wherein at least a portion of the at least one conductive surface is in the air path, an amplifier to amplify the measured one of voltage across or DC through the resistor, a processor to determine ion concentration based on the proportionality of the measured voltage across or DC through the resistor, wherein the proportionality is in a look up table in memory, at least one indicator configured to illuminate based on the magnitude of the voltage across or DC through the resistor, or wherein the indicator is a light.

This written description uses examples to disclose embodiments of the invention, including the best mode, and also to enable any person skilled in the art to practice embodiments of the invention, including making and using any devices or systems and performing any incorporated methods. The patentable scope of the invention is defined by the claims, and can include other examples that occur to those skilled in the art. Such other examples are intended to be within the scope of the claims if they have structural elements that do not differ from the literal language of the claims, or if they include equivalent structural elements with insubstantial differences from the literal languages of the claims.

The invention claimed is:

1. A method of measuring ion concentration in a defined space, the method comprising:
    disposing at least one conductive surface in a defined space;
    generating a flow of ions from an ion generator having an anode and a cathode into the defined space;
    measuring one of voltage across or direct current (DC) through a resistor connected between the cathode and the at least one conductive surface; and
    determining ion concentration in the defined space based upon a proportionality of ion concentration to the measured voltage or current.

2. The method of claim 1 wherein the proportionality of ion concentration is in a look up table, and the determining includes comparing the measured voltage or current to the look up table.

3. The method of claim 1 wherein a power supply to the ion generator includes a DC isolation barrier and the resistor is connected across the isolation barrier.

4. The method of claim 1 further comprising amplifying the measured voltage or current before determining ion concentration.

5. The method of claim 1 further comprising providing indication related to the magnitude of the voltage across or DC through the resistor.

6. The method of claim 5 wherein the providing indication comprises providing indication by way of indicator lights.

7. A device for measuring ion concentration in a defined space, comprising:
    a power supply;
    an ion generator having an anode and a cathode connected to the power supply;
    a fan to move air in a path between the anode and the cathode to a defined space;
    at least one conductive surface in the defined space;
    a resistor connected between the cathode and the at least one conductive surface; and
    a measuring circuit connected to the resistor for measuring one of voltage across or DC current through the resistor;
    wherein the measured one of voltage across or direct current (DC) through the resistor is proportional to ion concentration in the defined space.

8. The device of claim 7 further comprising a DC isolation barrier between the power supply and the ion generator, wherein the resistor is connected across the isolation barrier.

9. The device of claim 7 further comprising a display connected to the measuring circuit to indicate ion concentration in the defined space.

10. The device of claim 7 wherein at least a portion of the at least one conductive surface is in the path.

11. The device of claim 7 further comprising an amplifier to amplify the measured one of voltage across or DC through the resistor.

12. The device of claim 7 further comprising a processor to determine ion concentration based on the proportionality of the measured one of voltage across or DC through the resistor.

13. The device of claim 7 further comprising at least one indicator light configured to illuminate based on the magnitude of the voltage across or DC through the resistor.

* * * * *